US006942628B1

(12) United States Patent
Watson

(10) Patent No.: US 6,942,628 B1
(45) Date of Patent: Sep. 13, 2005

(54) OPEN CELL MESH CAST MATERIAL

(76) Inventor: Richard L. Watson, 1985 Cougar Trail, McPherson, KS (US) 67460

(*) Notice: Subject to any disclaimer, the term of this patent is extended or adjusted under 35 U.S.C. 154(b) by 18 days.

(21) Appl. No.: 10/751,597

(22) Filed: Jan. 5, 2004

Related U.S. Application Data

(63) Continuation of application No. 09/758,082, filed on Jan. 10, 2001, now Pat. No. 6,673,029.

(60) Provisional application No. 60/175,358, filed on Jan. 10, 2000.

(51) Int. Cl.$^7$ .............................. A61F 5/00; A61F 5/04
(52) U.S. Cl. ............................................. 602/8; 602/6
(58) Field of Search ....................... 602/5–8

(56) References Cited

U.S. PATENT DOCUMENTS

| | | | |
|---|---|---|---|
| 3,212,497 A | 10/1965 | Dickinson | |
| 3,745,998 A | 7/1973 | Rose | 128/89 |
| 3,930,496 A | 1/1976 | Gibbons | 128/90 |
| 3,998,219 A | 12/1976 | Mercer et al. | 128/89 |
| 4,060,075 A | 11/1977 | Blomer et al. | 128/90 |
| 4,294,240 A | 10/1981 | Thill | 128/156 |
| 4,442,833 A | 4/1984 | Dahlen et al. | 128/90 |
| 4,483,332 A | 11/1984 | Rind | 128/89 |
| 4,516,572 A | 5/1985 | Schlein | 128/156 |
| 4,683,877 A | 8/1987 | Ersfeld et al. | 128/90 |
| 4,841,958 A * | 6/1989 | Ersfeld et al. | 602/8 |
| 4,856,502 A | 8/1989 | Ersfeld et al. | 128/90 |
| 5,461,885 A | 10/1995 | Yokoyama et al. | 66/170 |
| 5,584,800 A | 12/1996 | Scholz et al. | 602/6 |
| 5,807,295 A * | 9/1998 | Hutcheon et al. | 602/42 |
| 5,836,902 A | 11/1998 | Gray | 602/5 |
| 6,063,980 A | 5/2000 | Peterson et al. | 602/49 |
| 6,074,354 A | 6/2000 | Scholz et al. | 602/6 |
| 6,093,161 A | 7/2000 | Vlaeyen et al. | 602/6 |
| 6,100,206 A | 8/2000 | Scholz et al. | 442/42 |
| 6,673,029 B1 * | 1/2004 | Watson | 60/6 |

OTHER PUBLICATIONS

Product Brochure from W. L. Gore & Associates, Inc., Procel Cast Liner, *The Cast You Can Wet* (Jun. 2001).
Product Brochure from Orthofix, Inc., *VACO®PED/VACO®ACHILL*, The Self-Fitting Vacuum Brace System for Foot and Ankle and Functional Treatment of Achillies Tendon Rupture (Jan. 2001).

* cited by examiner

*Primary Examiner*—Kim M. Lewis

(57) ABSTRACT

An orthopedic casting material made from layers of resin impregnated fiberglass fibers that are shaped, cut, and formed into a skeletal hexagonal cellular mesh array. The material forms a sheet with an array of aligned apertures that permit the flow of air. The size of the apertures may vary but is generally large in comparison to the fiberglass sections that define the sides of the apertures. The mesh may optionally include reinforcing strands and a lining. The material may be cut and trimmed in both its pliable and rigid states. The apertures additionally serve to receive the fingers or toes of the individual receiving the cast. The apertures also serve to allow continuous monitoring of the condition of the patient's skin. The skeletal structure of the material reduces the weight of the cast without sacrificing strength and protection.

8 Claims, 2 Drawing Sheets

OPEN CELL MESH CAST MATERIAL

RELATION TO OTHER APPLICATIONS

The present application is a continuation of U.S. patent application Ser. No. 09/758,082, filed Jan. 10, 2001, now U.S. Pat. No. 6,673,029 and claims the benefit of the filing date of U.S. Provisional Patent Application Ser. No. 60/175,358 filed Jan. 10, 2000, each of which is incorporated herein by reference.

BACKGROUND OF THE INVENTION

1. Field of the Invention

The present invention relates generally to structures and materials used in the formation of orthopedic casts. The present invention relates more specifically to a layered, open cell, fabric material impregnated with a curable polymer or pre-polymer resin that may be shaped and formed prior to curing into a rigid cast.

2. Description of the Related Art

Orthopedic casting materials have evolved over time from the earlier plaster of Paris and cotton gauze based casts to the more recent synthetic orthopedic casting tapes. Plaster of Paris based casts suffered from many difficulties that included being generally air impermeable, being subject to deterioration in contact with water, and being very heavy and bulky. The basic structure of the more recent synthetic casts involves a fabric sheet or tape, usually of fiberglass, that is impregnated with a liquid resin that cures and hardens in air over a short period of time. Alternate materials include thermoplastic resins that are formable at a temperature higher than room temperature but not so high as to be uncomfortable to the patient or the individual putting the cast material in place. In either case the result is a strong, relatively lightweight cast that, after curing, is not subject to deterioration in contact with water.

Fiberglass/Polymer Resin based cast materials typically come in two structural forms. The basic form involves a roll of tape anywhere from one to five inches wide that is applied by wrapping the tape around the limb to be cast. A second general structural form involves a pre-cut sheet of the material sized and shaped to fit around a specific appendage such as a wrist and forearm or an ankle and foot. The latter configuration is typically easier to apply but less conformable to the variety of sizes and shapes of limbs. The former structure (tape) is more versatile but is generally more difficult to apply.

The optimal characteristics of casting materials can be countervailing or conflicting in many cases. Obviously the material must result in a cast of sufficient strength to protect the healing limb. There is also however the desire for the cast to be lightweight and less bulky. As indicated above, it is desirable for the casting material to be readily formable prior to curing so as to more closely support and guard the limb. The resin-based materials should not overly adhere to the patient's skin or to the hands or gloves of the individual putting the cast in place. It is also important for the material to be readily removable when the limb has healed. Finally the finished cast should be resistant to deterioration in contact with water (and perspiration and the like) but should also be breathable. Significant skin maceration and patient discomfort can occur as a consequence of deficiencies in breathability. It has been most difficult to provide a material that is sufficiently strong and at the same time is lightweight and breathable.

There have been many efforts to improve upon both the structures and substance of the basic fiberglass/polymer resin casting material. Some of these efforts have focused on the type of resin used and the benefits of specific compositions. Other efforts have focused on the structure of the foundation fabric and the benefits of specific weaves and fiber geometry. Various patents reflecting some of these efforts include the following:

U.S. Pat. No. 5,584,800 issued to Scholz et al. on Dec. 17, 1996 entitled METHOD OF ENCLOSING A BODY MEMBER USING AN APERTURED EXTRUDED SHEET describes an extruded casting sheet made of a low temperature thermoplastic polymer that is soft and pliable above about 90° C. The material described may also include filler associated with the resin to improve its handling characteristics.

U.S. Pat. No. 5,461,885 issued to Yokoyama et al. on Oct. 31, 1995 entitled SUBSTRATE FOR RETAINING A HARDENABLE COMPOSITION describes specific fabric knit structures that are impregnatable with hardenable resin by capillary action. The material described is directed to combining strength and good air permeability.

U.S. Pat. No. 4,856,502 issued to Ersfeld et al. on Aug. 15, 1989 entitled CURABLE RESIN COATED SHEETS HAVING REDUCED TACK describes a non-woven fiber material that leaves small apertures or openings in the fabric sheets. The focus of the patent, however, is on the incorporation of additive or bound lubricants in the resin to facilitate the application of the cast without undesirable adhesion.

U.S. Pat. No. 4,841,958 issued to Ersfeld et al. on Jun. 27, 1989 entitled NONWOVEN ORTHOPEDIC CASTING MATERIALS WITH APERTURES describes yet another foundation made of a non-woven stretchable fabric impregnated with a curable prepolymer resin. The fabric is made of fiber bundles that receive and retain the resin and which form small openings between the bundles that remain open after curing.

U.S. Pat. No. 4,683,877 issued to Ersfeld et al. on Aug. 4, 1987 entitled ORTHOPEDIC CASTING ARTICLE AND METHOD describes a pre-cut, shaped "blank" of layered cast material that includes an extensible woven fabric and a layer of extensible foam. The pre-cut casting blank is sized and shaped to fit a particular limb and is initially held in place (prior to curing) by a number of clips that secure an edge of the material to the surface of the material upon wrapping around the limb.

U.S. Pat. No. 3,998,219 issued to Mercer et al. on Dec. 21, 1976 entitled ORTHOPEDIC SPLINT AND METHOD FOR FORMING SAME describes a multi-layered cast material comprising a central cellular core and inner and outer layers that sandwich the core and which when cured are rigid and supportive. Optional layers of foam material may be placed between the core and the inner and outer layers to provide better interlock between the layers (to reduce shifting between the layers).

Although a number of the materials described in the above references have as their stated goal a certain amount of air permeability, such properties remain less than optimal given the small size (on the order of 1 mm or less) of the apertures formed. In addition, none of the above materials accomplish much in the way of significantly reducing the size and weight of the finished cast. In general it is the resin (in a cured state) that provides the structural strength to the cast it is also the resin that contributes the most to the weight of the cast. Because of this problem, prior efforts have greatly limited the size of the openings or apertures in the fabric in order to maintain a sufficient amount of hardenable resin dispersed throughout the cast tape or sheet.

SUMMARY OF THE INVENTION

It is therefore an object of the present invention to provide a material for use constructing orthopedic casts of the fiberglass and hardenable resin type that significantly reduces the size and weight of the resultant cast structure.

It is another object of the present invention to provide a material for use in forming orthopedic casts that incorporates apertures of a size, number and arrangement that significantly increases the amount of air flow through the cast in comparison to existing open mesh cast materials.

It is a further object of the present invention to provide an open mesh cast material that incorporates foundational fabric material compositions and additive hardenable resin compositions that are known and utilized in the art.

It is a further object of the present invention to provide an open mesh cast material that provides sufficient rigidity without increased weight and size. It is a related object to address the foregoing through cast materials having optimal geometries.

It is a further object of the present invention to provide a material for use in forming orthopedic casts that may be precut and partially preformed to accommodate standard limb sizes and shapes.

It is a further object of the present invention to provide a material for use in forming orthopedic casts that while providing a rigid protective enclosure for the injured limb, may still be easily removed through the use of scissors or cast saws.

It is a further object of the present invention to provide a material for use in forming orthopedic casts that incorporates a continuous hexagonal conduit array within which are positioned microbeads or the like and which when subjected to a negative pressure differential becomes rigid.

Other objects and advantages will be apparent to those of ordinary skill in the art from the following disclosure.

In fulfillment of these and other objectives the present invention provides a fiberglass and hardenable resin based orthopedic casting material made from layers of resin impregnated fiberglass fibers that are shaped, cut, or otherwise formed into a skeletal hexagonal cellular mesh array. The material forms a generally sheet-like element having an array of apertures there through to permit the flow of air through the cast as well as the visual and physical monitoring of the condition of the patient's injured limb. The size of the hexagonal apertures in the material may vary according to the specific application of the cast but is generally large in comparison to the cross sectional size of the fiberglass sections that define the sides of the hexagonal apertures. Reinforcing strand components, such as stainless steel and Kevlar® fibers may be incorporated into the casting material. Optionally the mesh may incorporate a lining that prevents the resin from adhering to the skin. The sheet-like material may be cut and trimmed both prior to application in its pliable state and subsequent to application in its rigid state. The apertures in the material serve to receive the fingers or toes of the individual receiving the cast in a manner that facilitates the application of the material. Furthermore, the apertures serve the primary purpose of allowing nearly complete air flow through the cast to permit the rapid drying of the cast and the skin after wetting occurs. The skeletal structure of the material greatly reduces the size and weight of the cast without unduly sacrificing strength and protection.

Further objects and advantages of the invention will be readily apparent to those skilled in the art from the following description taken in conjunction with the accompanying drawings. The drawings constitute part of this specification and include exemplary embodiments of the present invention and illustrate various objects and features thereof.

DETAILED DESCRIPTION OF THE PREFERRED EMBODIMENTS

The basic structure of the material of the present invention is characterized by a specific geometry that is determined to provide the strength and rigidity necessary for an orthopedic cast while at the same time decreasing the weight and overall discomfort of the cast. In fulfilling these goals, variations on the specific geometric shapes involved and variations in the diametrical measurements of the structures are anticipated. The following description therefore provides but a few of the best examples of the application of the structures and the materials of the present invention.

Figure 1:
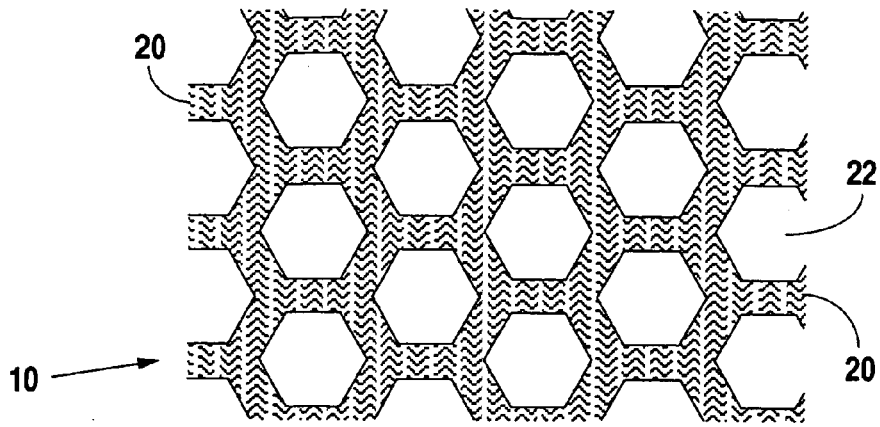
FIG. 1 is a plan view of a section of the material of the present invention.

Reference is made first to FIG. 1 for a brief description of the basic structure of open cell mesh fabric 10 comprising the material of the present invention. Mesh fabric 10, in its fundamental configuration, is a screen or mesh formed from layers of resin impregnated fiberglass fibers 20 that are shaped, cut, or otherwise formed into a skeletal hexagonal cellular array. This construction forms the hexagonal apertures 22 between fiber bundles 20. The actual layered structure of mesh fabric 10 is described in more detail below with respect to FIG. 2.

The construction of mesh fabric 10 may be accomplished according to a number of different, equally appropriate, methods. In a first method, layered bundles of fiberglass material (the construction of which is described in more detail below) may be woven into the hexagonal configuration shown in FIG. 1. A variety of fiber bundle weaving and knotting methods are known in the fabric industry that would create apertures similar to those shown in FIG. 1. A second method involves the cutting of a layered sheet of fiberglass material in a manner that creates hexagonal apertures 22 by the removal of a hexagonal section of the layered sheet material. In either case, the result is an open cell mesh fabric having relatively large hexagonal apertures there through. The connecting skeleton of the fabric is comprised of resin impregnated fiber bundles.

As indicated above, there are a number of different materials that are suitable for both the foundation of the open cell mesh fabric 10 and the resin that impregnates the fibers of the mesh fabric. Fiberglass fiber bundles or fabric materials, as are known in the art, provide the basic foundation in the preferred embodiment of the present invention. The structure of the present invention lends itself to use with a variety of resins that include both prepolymer resins that cure upon exposure to air and thermoplastic resins that are pliable above certain elevated temperatures. As indicated, there are many different resins well known in the art that appropriately flow by capillary action in between the fibers of the fiberglass fabric material and provide sufficient rigidity when cured or cooled to establish a hard and protective cast material.

Figure 2:
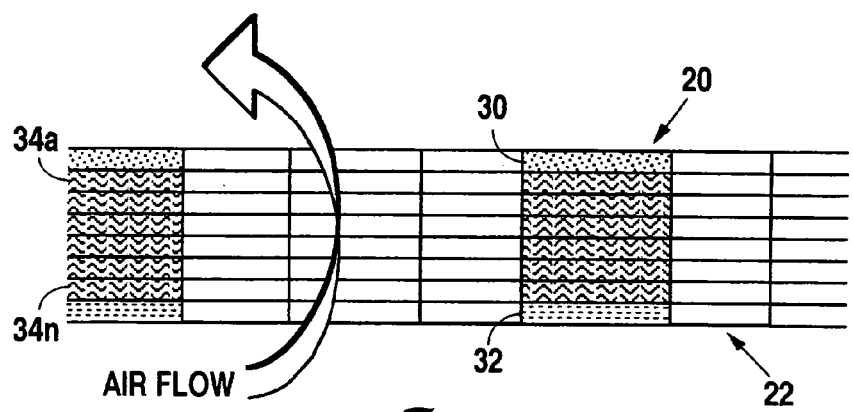
FIG. 2 is a detailed cross sectional view of the multi-layer structure of the material of the present invention.

Reference is now made to FIG. 2 for a detailed description of the layered construction of resin impregnated fiber bundles 20 shown externally in FIG. 1. In FIG. 2, the thickness dimension of the mesh fabric has been exaggerated with respect to the longitudinal dimensions of the mesh fabric, in order to clearly show the various layers in the construction of the fabric. In FIG. 2 a plurality of resin impregnated fiberglass layers 34a through 34n are shown as forming the core of the mesh fabric material. In the preferred embodiment there are 6–12 layers of fiberglass material which form a "bundle" core of about 5–15 mm in thickness. A layer of synthetic breathable material 30 is adhered to a "top" surface of the mesh fabric material and a breathable but water impermeable layer 32 is adhered to a second or "bottom" surface of the mesh fabric material. Layer 32 is intended to come into contact with the skin of the patient to which the cast is applied and therefore is intended to provide a nonabrasive surface. Commonly available materials such as Goretex® Cast Liner or the like are appropriate for use on this lower layer of the mesh fabric that comes in contact with the patient. The upper layer of synthetic breathable material 30 is positioned on the mesh fabric primarily for the purpose of easing the application of the cast material prior to its hardening.

In the cross sectional view shown in FIG. 2, resin impregnated fiberglass bundles 20 are shown in diametrical cross sections as are hexagonal apertures 22. In this view, it can be seen how air flow moves through aligned hexagonal apertures 22 between resin impregnated fiber bundles 20.

A modification of the cross sectional structure shown in FIG. 2 is anticipated wherein top layer 30 and bottom layer 32 extend around the plurality of fiberglass layers 34a–34n so as to effectively enclose the fiberglass material. Top layer 30 and bottom layer 32 may be sealed or sewn together where their edges meet. This modification reduces the exposure of the sometimes abrasive edge of the fiberglass material after hardening.

Figure 3:
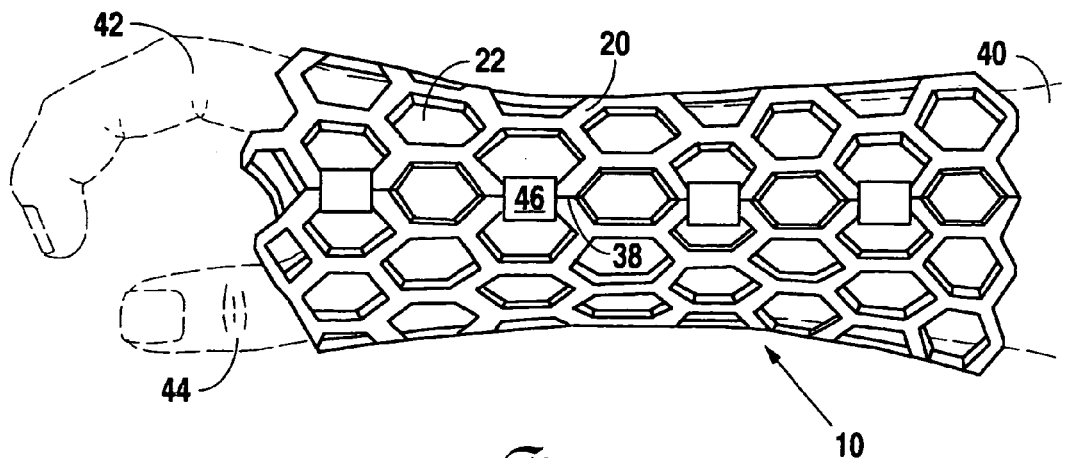
FIG. 3 is a perspective view of a typical application of a section of the material of the present invention as used in conjunction with the formation of a wrist and forearm cast.

Reference is now made to FIG. 3 for a description of the manner in which a section of the cast material of the present invention is positioned and fixed on an injured limb of a patient. The limb section shown in FIG. 3 is that of a patient's forearm 40 and includes the patient's hand 42 and the patient's thumb 44. In this view, a section 10 of open cell mesh fabric of the present invention has been cut and configured to form around the forearm 40, wrist (not shown), hand 42, and thumb 44 of the patient. The hexagonal structure of the open cell mesh fabric 10 can be clearly seen both in its relative shape and size with respect to the human hand.

In the preferred embodiment of the present invention, the diametrical cross section of resin impregnated fiber bundles 20 is in the range of 0.5 to 1.5 centimeters. The diametrical cross section of hexagonal apertures 22 in the preferred embodiment is in the range of 2.5 to 4.5 centimeters. This diametrical measurement for the hexagonal apertures is an average between the wall-to-wall diameter and the apex-to-apex diameter of the hexagonal shape.

The mesh fabric section shown in FIG. 3 has been cut into a generally rectangular shape having a first dimension equal to the length of the area to be covered along the patient's forearm, wrist and hand. The second dimension for the rectangular section comprises approximately 80%–100% of the maximum circumference around the patient's forearm, wrist and hand in an injured condition. In this manner, the rectangular section readily covers the injured area, providing sufficient support above and below the injured area on the limb, and provides the ability to gradually "close" the cast once the rectangular section has been initially wrapped around the limb. It is recognized that the circumference of an injured limb is frequently greater than that of the healed limb. For this reason it is anticipated that a gap on the order of 2.5 cm may be left between the edges of the material once it has initially been wrapped around the limb. The closure clips, described below, permit the gradual closure of the cast as swelling of the limb reduces over time.

One benefit of the open cell hexagonal structure of the present invention is to provide an aperture through which the thumb or other small appendage of the patient may be passed in order to secure the initial placement of the material on the patient. Application of the material would therefore comprise passing the thumb 44 (and in some cases the individual fingers of the patient's hand 42) through a selection of appropriate hexagonal apertures 22 in the mesh fabric material. This provides an initial means for securing the material to the patient and allows the remaining portion of the material to be drawn securely around the limb. In the view shown in FIG. 3, the initial (first positioned) edge of the mesh fabric material 10 is secured by attachment to the thumb 44 as described above and then wrapped over the wrist and forearm (into the drawing page), around the wrist and forearm (and then out from the drawing page), to end at the point shown on the near side of the patient's wrist and forearm. Leading edge 38 of the cast material is shown just meeting the initially placed layer of cast material and secured thereto by a number of cast clips 46 which are described in more detail below. The open cell hexagonal structure of the material of the present invention provide readily accessible apertures through which the cast closure clips may be placed. These closure clips 46 are structured so that they may progressively draw the cast closed even after the resin in the cast material has hardened. The cured or hardened fiberglass/resin material remains flexible enough to follow the reduced circumference of the limb as it heals under the progressive closure of the closure clips.

It is anticipated that a variety of preformed, precut shapes of the material of the present invention might be used for standard cast locations such as that shown in FIG. 3. Similar applications to ankles, elbows, hands, feet and lower leg sections are anticipated. In conjunction with these "custom" shapes, specifically placed appendage apertures may be cut or formed into the cast material. These appendage apertures may be specifically positioned, sized and shaped as appropriate for the finger, thumb, toe or other appendage they are intended to engage. Alternately, sufficiently large "blanks" of the material may be provided with the caregiver cutting and forming the material to the needed area prior to application. Depending upon the type of hardenable resin utilized, it is anticipated that a large sheet of the material of the present invention may be placed around the injured limb area on the patient and then trimmed to an appropriate size and shape before the hardening process is initiated.

Figure 4:
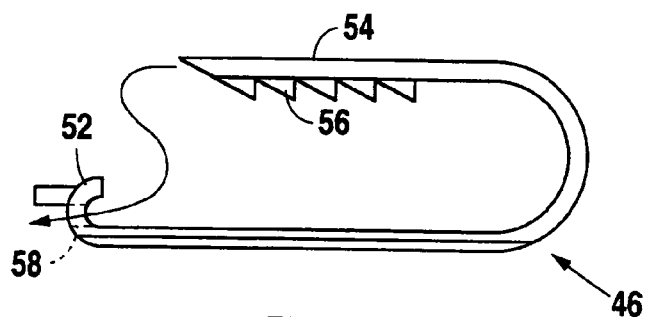
FIG. 4 is a detailed view of a clip used in association with the application of the material of the present invention.

The structure of the cast clip or closure 46 shown in FIG. 3 is described in more detail with respect to FIG. 4. The clip 46 shown in FIG. 4 is but one example of an appropriate device for securing leading edge 38 of the cast material back onto an adjacent, overlapped section of the cast material. Clip 46 in FIG. 4 is comprised of a polymer plastic strap having a first end 52 with aperture 58 therein that is designed to receive and engage a second end 54 that incorporates a plurality of barbs 56. Clips of this type that incorporate a number of barbs so as to secure the clip in a number of degrees of closure are well known in the art. Although the closure shown in FIG. 4 is structured to accommodate the hexagonal apertures in the preferred embodiment, alternate types of cable tie wrap closures may be used.

The above-described preferred embodiment of the present invention makes use of fabric materials whose chemical compositions are well known in the art. Likewise, the resins used, as described herein, are well known and have characteristics desirable for the formation of orthopedic casts. Again, it is the geometries and dimensions of the structures formed from these compositions that are described in the present invention and which address many of the problems present in the prior art. Although a hexagonal geometry has been described and emphasized herein, alternate geometries are anticipated. The hexagonal geometry provides a structure that is strong and stiff when subjected to forces from many directions. The hexagonal geometry also maximizes strength while limiting the amount of skeletal structure. Other aperture and bridge geometries are anticipated that meet these same objectives. Alternative compositions that utilize the same geometries and dimensions are further anticipated by the present invention.

Figure 5:
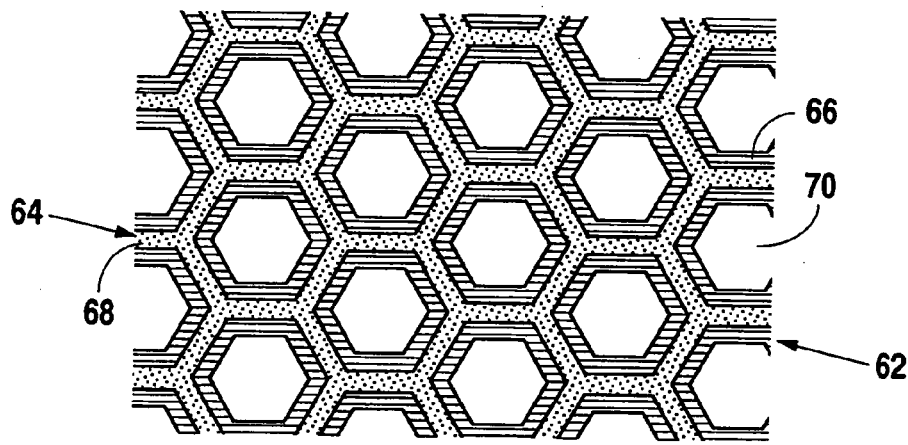
FIG. 5 is a plan view of an alternative embodiment of the material of the present invention.
Figure 6:
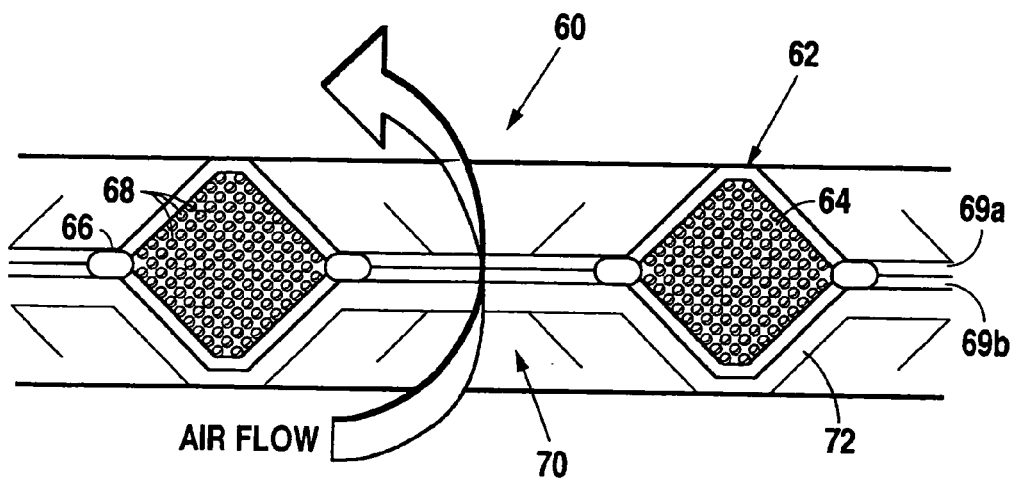
FIG. 6 is a detailed cross sectional view of the alternative embodiment shown in FIG. 5.

FIGS. 5 and 6 provide a second example of the application of the geometries and dimensions of the open mesh material of the present invention, constructed with alternate elements. FIG. 5 is similar to the view shown in FIG. 1 but with the alternative compositions mentioned. It is known in the art of splints and casts that a layered sheet of material comprising a core of microbeads contained within a polymer envelope may be subjected to a vacuum that removes most of the air surrounding the microbeads and thereby forms a relatively rigid structure that is maintained as long as a negative pressure differential is maintained. Typically, such microbead technologies are utilized in large sheets that are initially pliable and subsequently are flat and firm after being subjected to a vacuum. In the present invention, this basic structure and technology is implemented in the manner shown in FIG. 5. This external view shows open cell mesh sheet material 60 made up of an array of channeled sections 62 whose cross sectional structure is described in more detail below.

These channeled sections 62 comprise interior channel 64 which is bounded on either side by sealed seam 66. In this manner, a continuous hexagonal array of conduit is formed between two layers of polymer sheets 69a and 69b. Within the open conduit thus formed are positioned a plurality of microbeads 68. The composition and size of microbeads 68 may vary and is not particularly important in the present application. Such microbeads and evacuation layers are well known in the art and the compositions and sizes as commonly used in the field are appropriate here.

The construction shown in FIG. 5 forms the same hexagonal aperture 70 as is formed in the first described preferred embodiment. Seams 66 are exaggerated in FIG. 5 in order to clarify the position of the open channel contained between the layers of the polymer sheet material.

Reference is now made to FIG. 6 for a description of the cross sectional structure of the web shown generally in FIG. 5. Channel section 62 is seen to be comprised of two layers of polymer sheeting 69a and 69b that are sealed together into the form shown in FIG. 5. This sealing process creates the open channels 64 within which microbeads 68 are placed. The process typically involves placement of the microbeads and then heat sealing the layers together over the beads. Alternately, the layers may be sealed together with the beads introduced into the open volume there between. Typically, hexagonal aperture 70 would be cut through the layers of the material after the sealing process has been carried out.

Microbeads 68 generally fill the open channel 64 in a loose packed manner prior to the evacuation of air from the channel. In this state, the web material created is pliable and formable around the limb of the patient much in the same manner as described above in FIG. 3. Once positioned around the limb of the patient, evacuation of the channels with an appropriate vacuum pump through a valve structure (not shown) creates a rigid skeleton structure similar in many respects to the rigid structure formed by the hardenable resin in the first described embodiment. As long as a negative pressure differential is maintained, rigidity of the structure is maintained. As with the layered structure shown in FIG. 2, it is desirable to have a less abrasive layer 72 positioned on the inside or lower surface of the cast material. This surface, which comes in contact with the patient, is preferably layered with a breathable but water impermeable material.

Although the present invention has been described in conjunction with first and second preferred embodiments, it is anticipated that a variety of other compositions for the foundational fabric material and the hardenable additive to the foundation, are possible. The important elements of the present invention include the cellular geometry of the open mesh fabric and the generally larger dimensions of the apertures thereby formed. A variety of compositions for both the foundational fabric and the hardenable material are anticipated.

I claim:

1. A material for the formation of an orthopedic cast, said material pliable and formable prior to and during application and hardenable after application, said material comprising:
   a mesh fabric comprising a plurality of layers of fibers defining a honeycomb skeletal array of aligned hexagonal cells passing through said plurality of layers; and
   a quantity of hardenable resin positioned in association with said fibers, said resin pliable and formable in a first condition and hardened in a second cured condition;
   wherein said material may be wrapped and molded around an injured extremity in said first pliable condition and may serve as a cast structure in said second cured condition.

2. The material of claim 1 further comprising a lining layer positioned adjacent said mesh fabric and between said mesh fabric and the skin of said injured extremity, said lining layer comprising a breathable hydrophilic close weave fabric.

3. The material of claim 1 wherein said mesh fabric comprises fiberglass fiber bundles having interstitial space between said fibers and wherein said resin generally fills said interstitial space.

4. The material of claim 1 wherein said hexagonal cells have a diametrical dimension generally large in comparison to the cross sectional dimension of said fiber bundles.

5. The material of claim 4 wherein said diametrical dimension of said hexagonal cells is in the range of 2–8 centimeters and said cross sectional dimension of said fiber bundles is in the range of 0.5–1.5 centimeters.

6. The material of claim 1 further comprising reinforcing strand components incorporated into said mesh fabric.

7. The material of claim 6 wherein said reinforcing strand components comprise stainless steel.

8. The material of claim 6 wherein said reinforcing strand components comprise synthetic fibers.

* * * * *